(12) United States Patent
Tanio et al.

(10) Patent No.: US 7,594,905 B2
(45) Date of Patent: Sep. 29, 2009

(54) SANITARY NAPKIN HAVING THREE-DIMENSIONAL STRUCTURE

(75) Inventors: Toshiyuki Tanio, Kagawa (JP); Wataru Yoshimasa, Kagawa (JP); Kenichiro Kuroda, Kagawa (JP); Shinobu Fujikawa, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 293 days.

(21) Appl. No.: 11/124,561

(22) Filed: May 5, 2005

(65) Prior Publication Data
US 2005/0267434 A1 Dec. 1, 2005

(30) Foreign Application Priority Data
May 27, 2004 (JP) ............... 2004-156961

(51) Int. Cl.
*A61F 13/15* (2006.01)
*A61F 13/20* (2006.01)
(52) U.S. Cl. .............. 604/385.27; 604/380; 604/385.31
(58) Field of Classification Search ............ 604/385.17, 604/385.01, 385.04, 378–380, 385.101
See application file for complete search history.

(56) References Cited
U.S. PATENT DOCUMENTS

| | | | | |
|---|---|---|---|---|
| 4,804,380 A | * | 2/1989 | Lassen et al. .......... | 604/385.17 |
| 5,558,656 A | * | 9/1996 | Bergman ................ | 604/385.23 |
| 5,591,148 A | * | 1/1997 | McFall et al. ............... | 604/378 |
| 6,210,385 B1 | * | 4/2001 | Mizutani ................ | 604/385.01 |
| 6,394,989 B2 | * | 5/2002 | Mizutani ................ | 604/385.01 |
| 6,578,948 B2 | * | 6/2003 | Kashiwagi et al. .... | 604/385.101 |
| 7,156,832 B2 | * | 1/2007 | Drevik et al. .......... | 604/385.31 |

FOREIGN PATENT DOCUMENTS

| | | |
|---|---|---|
| JP | 11-042250 | 2/1999 |
| JP | 2000-083994 | 3/2000 |
| JP | 2002-320638 | 11/2002 |

OTHER PUBLICATIONS

Patent Abstracts of Japan for 2003-10240 published on Jan. 14, 2003.
Derwen WPI: English Abstract for EP 1269953 A2.

* cited by examiner

*Primary Examiner*—Michele Kidwell
(74) *Attorney, Agent, or Firm*—Darby & Darby P.C.

(57) ABSTRACT

A sanitary napkin includes a napkin body containing a liquid absorbent layer and a three-dimensional structure is disposed on the skin-side surface of the napkin body. The three-dimensional structure is formed of a reinforcing member and a liquid-permeable sheet, and an elastic member is disposed along an apex to extend in a longitudinal direction. The reinforcing member has high-density portions and low-density portions alternating with each other in the longitudinal direction so that the apex can be shortened in the longitudinal direction by an elastic contractive force of the elastic member. Therefore, the napkin body can be easily kept curved.

3 Claims, 11 Drawing Sheets

SANITARY NAPKIN HAVING THREE-DIMENSIONAL STRUCTURE

BACKGROUND OF THE INVENTION

1. Field of the Invention

The present invention relates to a sanitary napkin having a three-dimensional structure intended to come into contact with at least one of the vagina and the intergluteal cleft, which extends posteriorly from the anus of the wearer's body, and more particularly to a sanitary napkin whose napkin body can be easily kept curved to conform to the contour of the wearer's body while the three-dimensional structure is kept in contact with the wearer's body.

2. Description of the Related Art

Conventional sanitary napkins include ones having a protruding structure, which is intended to come into close contact with the wearer's body, on a skin-side surface of a napkin body containing a liquid absorbent layer.

Patent Publication 1 identified below discloses a sanitary napkin in which a longitudinally extending elastic member is provided between a liquid absorbent layer and a topsheet covering the skin-side surface of the liquid absorbent layer. The elastic member exhibits an elastic contractive force to bring front and rear edges of the sanitary napkin closer to each other, so that the sanitary napkin is curved to have its skin-side surface recessed and also the center of the topsheet is lifted away from the liquid absorbent layer because of the elastic member. By keeping the topsheet thus lifted away from the liquid absorbent layer in close contact with the wearer's body, menstrual blood is allowed to be absorbed by the liquid absorbent layer via the topsheet.

Patent Publication 2 identified below discloses a sanitary napkin in which a three-dimensional structure, which is formed of a liquid-permeable sheet to have a T-shaped cross-section, is provided on the skin-side surface of a napkin body. The three-dimensional structure is provided with elastic members for exhibiting a longitudinal contractive force. These elastic members exert a force to bring front and rear edges of the napkin body closer to each other so that the napkin body is curved, which makes the three-dimensional structure rise from the skin-side surface of the napkin body. This three-dimensional structure can be kept in close contact with the female genital organ and is aimed at providing a pleasant feeling during wear.

Patent Publication 3 identified below discloses a sanitary napkin including a primary absorbent member of a triangular cross-section. This primary absorbent member is composed of an absorbent core for absorption and retention of liquid and an outer cover covering the absorbent core. In this sanitary napkin disclosed in Patent Publication 1, the primary absorbent member comes into close contact with the vaginal opening so that menstrual blood can be mainly absorbed and retained by the primary absorbent member. The sanitary napkin also includes a secondary absorbent member which is flat and intended to come into contact with garments and the primary absorbent member is disposed on the secondary absorbent member.

Patent Publication 4 identified below discloses a sanitary napkin including a tube of absorbent material having a function of absorbing liquid. This tube of absorbent material is composed of an absorbent material shaped into a tube and a cover covering the absorbent material and therefore the tube of absorbent material is allowed to comfortably fit to the vaginal opening of a wearer. Here, the tube of absorbent material is disposed on a base pad.

Patent Publication 5 identified below discloses a hump of a triangular cross-section bulging from a skin-side surface of a sanitary napkin. This hump is composed of an absorbent body and a stiffening element disposed between a liquid-permeable topsheet and a liquid absorbent layer, and the stiffening element is formed of a rigid material such as a plastic sheet. Even when the hump reinforced by the stiffening element comes into contact with the vaginal opening and is subjected to a compressive force due to body pressure, the hump can keep the sanitary napkin in close contact with the vaginal opening without being crushed down.

Patent Publication 6 identified below discloses a sanitary napkin having a heaped protrusion in a rear region of a skin-side surface. From the description of Patent Publication 4, it is unclear how the protrusion is constituted, but it describes that the protrusion comes into contact with the cleft of the buttocks to prevent rearward leakage of menstrual blood.

Patent Publication 1: Japanese Unexamined Patent Publication No. 2000-83994
Patent Publication 2: Japanese Unexamined Patent Publication No. 2002-320638
Patent Publication 3: Japanese Unexamined Patent Publication No. H11-500940
Patent Publication 4: Japanese Unexamined Patent Publication No. 2002-512851
Patent Publication 5: Japanese Unexamined Patent Publication No. 2001-504727
Patent Publication 6: Japanese Unexamined Patent Publication No. H11-42250

In either of the sanitary napkins disclosed in Patent Publications 1 and 2, the three-dimensional structure is formed to bulge from the skin-side surface of the napkin body for coming into contact with the vaginal opening, but the sheet forming the three-dimensional structure does not have a sufficient stiffness in itself to maintain the shape of the three-dimensional structure. The three-dimensional structure is kept bulging by string-like elastic members that exhibit an elastic contractive force in the longitudinal direction.

Accordingly, when the three-dimensional structure is in contact with the vaginal opening, a wearer may sense a local pressure due to tension of the elastic members to cause an unpleasant feeling. Therefore, it is necessarily required to set the tension of the elastic members to a relatively low level. Since the three-dimensional structure in which the tension of the elastic members is set to a relatively low level tends to come into soft contact with the wearer's body, it is suitable for coming into close contact with the vaginal opening, but does not have a sufficient stiffness to enable intrusion into the intergluteal cleft, which extend posteriorly from the anus. Hence, the three-dimensional structure cannot be brought into close contact with the intergluteal cleft and becomes less effective in preventing menstrual blood from flowing down the intergluteal cleft posteriorly during sleep.

In the sanitary napkins disclosed in Patent Publications 3 to 5, on the other hand, the three-dimensional structure disposed on the skin-side surface of the napkin body has the absorbent. In the sanitary napkins where the absorbent is disposed on the skin-side surface of the napkin body, however, when the napkin body is curved to fit the wearer's body from the crotch to the buttocks, the three-dimensional structure is longitudinally contracted to exhibit a repulsive force against compression. Accordingly, the sanitary napkin worn on the wearer's body tries to recover to its original flat shape, which easily creates a clearance between the skin-side surface of the napkin body and the wearer's body.

Particularly in the sanitary napkin disclosed in Patent Publication 5, since the three-dimensional structure contains the rigid material such as a plastic sheet, the rigid material interferes with the curvature of the napkin body. In addition, a wearer tends to feel uncomfortable when the rigid material comes into contact with the wearer's body.

In the sanitary napkin disclosed in Patent Publication 6, on the other hand, although the structure of the protrusion is unclear, the protrusion appears to function to interfere with the curvature of the napkin body in the same manner as those disclosed in Patent Publications 3 to 5.

SUMMARY OF THE INVENTION

The present invention has been developed to solve the problems in the prior art set forth above and has an object to provide a sanitary napkin whose napkin body can be easily curved to conform to the contour of the wearer's body from the crotch to the buttocks so that a clearance will not be easily created between the wearer's body and a napkin body in a state where a three-dimensional structure provided on the skin-side surface of the napkin body is kept in close contact with the wearer's body.

The present invention has another object to provide a sanitary napkin whose three-dimensional structure can be kept in close contact with the intergluteal cleft so as to be effective in preventing rearward leakage of menstrual blood.

According to the present invention, there is provided a sanitary napkin comprising a napkin body containing a liquid absorbent layer for absorption and retention of liquid and a three-dimensional structure disposed on a skin-side surface of the napkin body, wherein the three-dimensional structure has a reinforcing member which functions to keep the three-dimensional structure bulging from the skin-side surface of napkin body and is allowed to be deformed by a load exerted on the three-dimensional structure, wherein when front and rear ends of the three-dimensional structure are brought closer to each other with the skin-side surface of the napkin body concavely curved, a length of the reinforcing member along an apex decreases more than a length of the reinforcing member along the skin-side surface of the napkin body.

Since the three-dimensional structure is relatively stiff, the sanitary napkin is allowed to come into close contact with the vaginal opening or the intergluteal cleft. Moreover, since the three-dimensional structure is allowed to be deformed by a pressure from above, the three-dimensional structure is less apt to give an unpleasant feeling to the vaginal opening or the intergluteal cleft. Furthermore, since the three-dimensional structure is constructed to allow the apex to be shortened longitudinally, the napkin body can be easily curved to conform to the contour of the wearer's body from the crotch to the buttocks when the three-dimensional structure is in close contact with the wearer's body. Therefore, the napkin body can be easily kept in close contact with the wearer's body.

According to one embodiment of the present invention, the reinforcing member may have high-density portions and low-density portions having a lower density than the high-density portions and alternating with the high-density portions in a longitudinal direction of the sanitary napkin, and the high-density portions may be allowed to be brought closer to each other along the apex by deformation of the low-density portions to thereby decrease the length of the reinforcing member along the apex.

According to another embodiment of the present invention, the reinforcing member may have a plurality of cut-outs spaced apart in the longitudinal direction of the sanitary napkin, and a longitudinal opening size of the individual cut-outs may gradually increase toward the apex.

In either case, preferably, an elastic member is provided to shorten the apex of the reinforcing member in the longitudinal direction of the sanitary napkin. This elastic member facilitates the curvature of the napkin body.

It is also preferred that the reinforcing member forms two walls opposing in a width direction of the sanitary napkin with a hollow therebetween. With a hollow inside the three-dimensional structure, the three-dimensional structure can be easily deformed when it enters the intergluteal cleft and is subjected to a pressure which the buttocks of a wearer exert on the two walls.

It is also preferred that the reinforcing member is formed of a fibrous layer and a skin-side surface of the reinforcing member is covered with a liquid-permeable sheet. With the reinforcing member being formed of a fibrous layer, menstrual blood adhered to the three-dimensional structure can be easily retained by the reinforcing member and then readily transferred to the liquid absorbent layer of the napkin body.

It is also preferred that the napkin body is elongated to have a vagina-facing region and an intergluteal cleft-facing region rearward of the vagina-facing region and the three-dimensional structure is provided at least in the intergluteal cleft-facing region.

Since the three-dimensional structure according to the present invention can be easily kept bulging from the skin-side surface of the napkin body and its apex can be easily curved, the three-dimensional structure is allowed to easily enter and come into close contact with the intergluteal cleft. Therefore, menstrual blood trying to move rearwardly of the napkin along the intergluteal cleft can be easily blocked.

BRIEF DESCRIPTION OF THE DRAWINGS

FIGS. 10(A) and 10(B) are partial perspective views showing a three-dimensional structure according to the third embodiment, wherein FIG. 10(A) shows a state where the sanitary napkin is flat while FIG. 10(B) shows a state where the sanitary napkin is curved;

FIGS. 11(A) and 11(B) are partial perspective views showing a modification of the three-dimensional structure according to the third embodiment, wherein FIG. 11(A) shows a state where the sanitary napkin is flat while FIG. 11(B) shows a state where the sanitary napkin is curved;

DESCRIPTION OF THE PREFERRED EMBODIMENT

Figure 1:
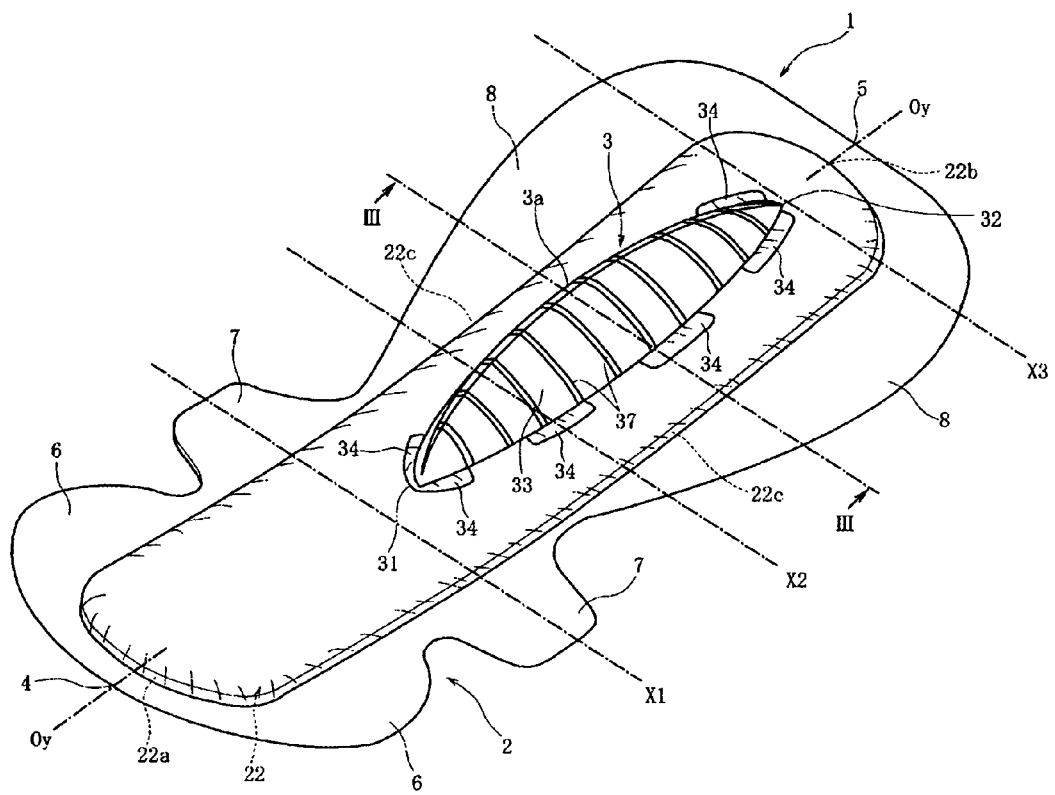
FIG. 1 is a perspective view showing a sanitary napkin according to a first embodiment of the invention.
Figure 2:
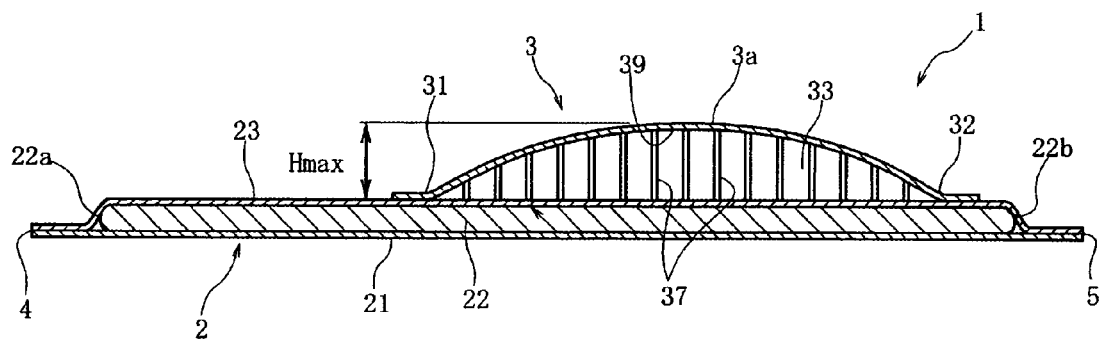
FIG. 2 is a longitudinal sectional view of the sanitary napkin.
Figure 3:
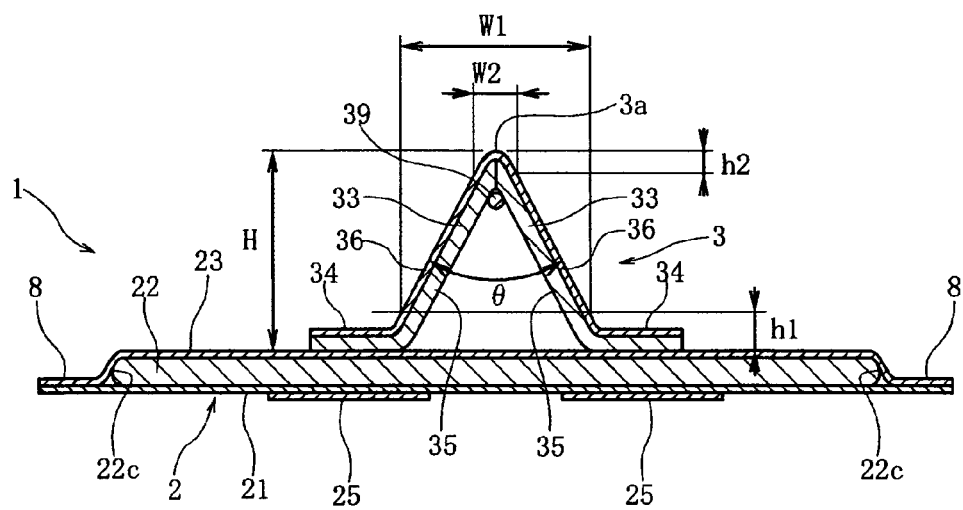
FIG. 3 is a sectional view of the sanitary napkin of FIG. 1 taken along line III-III.
Figure 4:
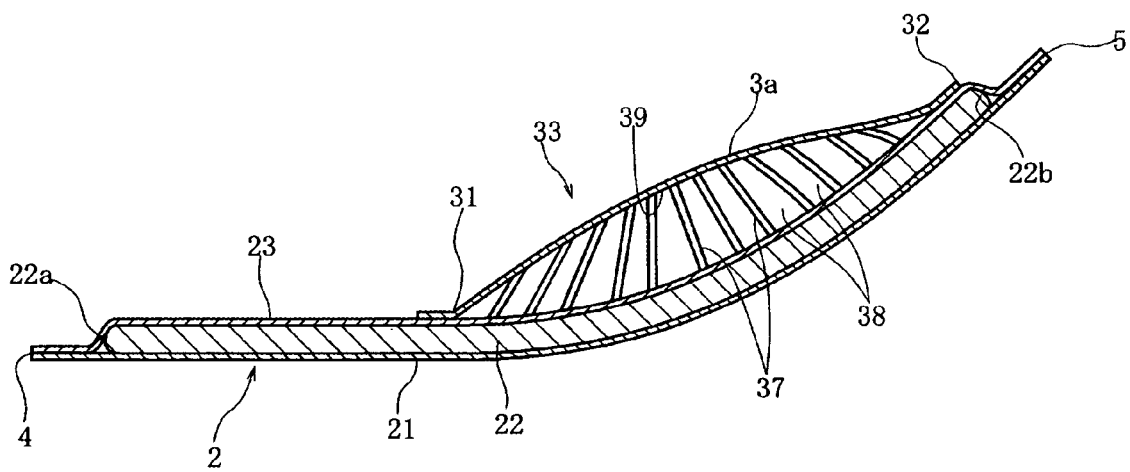
FIG. 4 is a longitudinal sectional view showing a state where the sanitary napkin according to the first embodiment is curved.
Figure 5A:
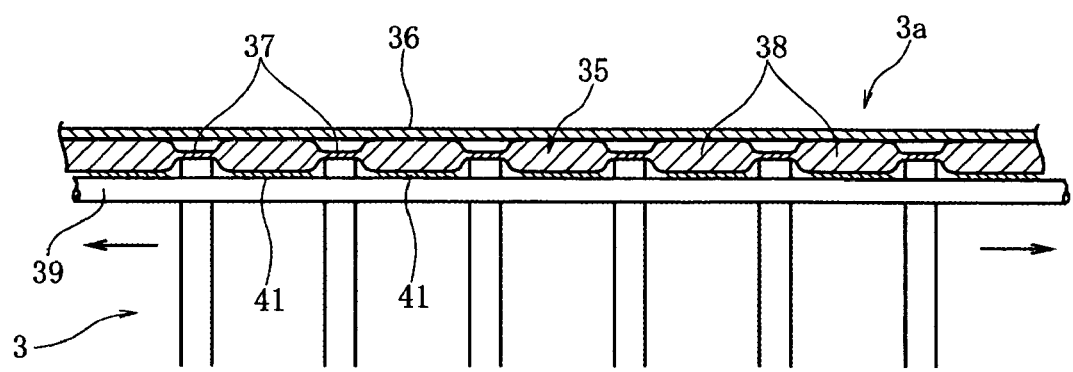
FIG. 5(A) is a partial longitudinal sectional view showing an apex of a three-dimensional structure when a napkin body is flat.
Figure 5B:
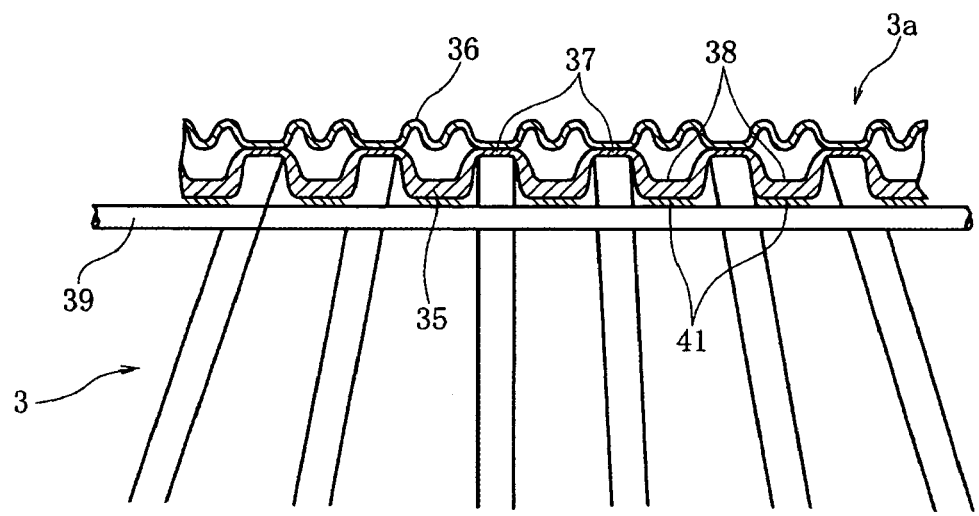
FIG. 5(B) is a partial longitudinal sectional view showing the apex when the napkin body is curved.

FIG. 1 is a perspective view showing a sanitary napkin 1 according to a first embodiment of the invention, FIG. 2 is a longitudinal sectional view of the sanitary napkin 1 in a flat state, and FIG. 3 is a transverse sectional view of the sanitary napkin 1 of FIG. 1 taken along line III-III. FIG. 4 is a longitudinal sectional view of the sanitary napkin 1 in a curved state. FIGS. 5(A) and 5(B) are partial longitudinal sectional views showing an apex of a three-dimensional structure in the flat state and the curved state, respectively.

It should be noted that the sanitary napkin, as well as its individual components, has two major surfaces: of which one surface intended to be worn toward the wearer's crotch is referred to as "skin-side surface", while the other surface is referred to as "garment-side surface". In addition, the lengthwise direction of the sanitary napkin is referred to as "longitudinal direction", while the direction perpendicular to the longitudinal direction is referred to as "width direction". With respect to dimensions of the individual components, unless otherwise stated, a dimension measured in the longitudinal direction is referred to as "length", while a dimension measured in the width direction is referred to as "width".

The sanitary napkin 1 according to the first embodiment comprises a napkin body 2 and a three-dimensional structure 3 located on the skin-side surface of the napkin body 2.

As shown in FIGS. 2 to 4, the napkin body 2 comprises a liquid blocking backsheet 21 on its garment-side surface, a liquid absorbent layer 22 disposed on it, and a liquid-permeable topsheet 23 covering the liquid absorbent layer 22.

As shown in FIG. 1, the napkin body 2 has a curved front end 4, as well as a curved rear end 5. The napkin body 2 is elongated to have a maximum length of 280 to 450 mm. The liquid absorbent layer 22 is also elongated, and the liquid absorbent layer 22 has a curved front end 22a spaced slightly inward from the front end 4 and a curved rear end 22b spaced slightly inward from the rear end 5. On the other hand, left and right side ends 22c, 22c of the liquid absorbent layer 22 extend linearly in parallel relationship with a longitudinal centerline Oy.

The napkin body 2 has front flaps 6, 6, fold-back flaps 7, 7 and rear flaps 8, 8 which project from the side ends 22c, 22c of the liquid absorbent layer 22. Here, the fold-back flaps 7, 7 are located rearward of the front flaps 6, 6 and the rear flaps 8, 8 are located rearward of the fold-back flaps 7, 7. In the front flaps 6, 6, fold-back flaps 7, 7 and rear flaps 8, 8, the backsheet 21 and the topsheet 23 overlap with each other and are bonded to each other through a hot-melt type adhesive. Alternatively, liquid blocking side sheets may be provided on the skin-side surface of the napkin body to cover both sides thereof so that the backsheet 21 and the side sheets constitute the front flaps 6, 6, fold-back flaps 7, 7 and rear flaps 8, 8.

The backsheet 21 may be a film, for example, a polyethylene resin film having a basis weight of about 30 g/m², and is preferably permeable to moisture. The liquid absorbent layer 22 may be a mixture of fluff pulp and superabsorbent polymer (SAP) wrapped in a hydrophilic tissue, wherein the fluff pulp has a weight of about 400 g/m².

The topsheet 23 may be a through-air bonded nonwoven fabric having a basis weight of about 20 g/m². Constituent fibers of the through-air bonded nonwoven fabric may be sheath/core bicomponent synthetic fibers, of which the core is polypropylene resin and the sheath is polyethylene resin and the core is mixed with an inorganic filler such as titanium oxide.

The liquid-permeable topsheet 23 may be a point-bonded nonwoven fabric, a spunlaced nonwoven fabric or a spunbonded nonwoven fabric, without limited to the through-air bonded nonwoven fabric, but its fiber density is preferably equal to or less than 0.12 g/cm³ so as to improve liquid permeability. Alternatively, the topsheet 23 may be a resin film formed with a large number of liquid passage apertures.

X1 shown in FIG. 1 represents a vagina-facing reference line and this vagina-facing reference line X1 is spaced 100 to 200 mm rearwardly from the front end 4 of the napkin body 2, for example, spaced about 150 mm rearwardly from the front end 4.

The vagina-facing reference line X1 as used herein is a target position with which the center of the vaginal opening is to almost coincide when the sanitary napkin 1 is fixed to an undergarment and worn in the crotch. Leading to this target is through the contour of the sanitary napkin as viewed from the skin side or the whole design including the shape of compression lines on the skin-side surface, and particularly when the fold-back flaps 7, 7 are provided as in the present embodiment, the longitudinal centers of the fold-back flaps 7, 7 usually coincide with the target with which the center of the vaginal opening is to coincide.

In the present embodiment, accordingly, the line passing through the centers of the fold-back flaps 7, 7 is taken as the vagina-facing reference line X1.

X2 shown in FIG. 1 represents an anus-facing reference line and this anus-facing reference line X2 is intended to face the anus when the vagina-facing reference line X1 coincides with the center of the vaginal opening. The anus-facing reference line X2 is usually spaced a distance of 30 to 70 mm, which varies depending on the wearer's body, rearwardly from the vagina-facing reference line X1.

X3 shown in FIG. 1 represents a coccyx-facing reference line. This coccyx-facing reference line X3 is intended to face the coccyx when the vagina-facing reference line X1 coincides with the center of the vaginal opening. The coccyx-facing reference line X3 is usually spaced a distance of 120 to 180 mm, which varies depending on the wearer's body, rearwardly from the vagina-facing reference line X1. The rear end 5 of the napkin body 2 and the rear end 22b of the liquid absorbent layer 22 are located rearward of the coccyx-facing reference line X3.

In the crotch of a woman, a "body's groove" extends from the anterior end of the vagina (the anterior end of the labia) to the coccyx, and of the "body's groove", the portion from adjacent the anus to the coccyx is referred to as "intergluteal cleft" throughout the description. In the sanitary napkin 1 of FIG. 1, the area within 50 mm forward and rearward from the vagina-facing reference line X1 is referred to as vagina-facing region, while the area from the anus-facing reference line X2 to the coccyx-facing reference line X3 is referred to as intergluteal cleft-facing region.

In the sanitary napkin 1, the three-dimensional structure 3 is provided mainly on a rear portion of the napkin body 2. The three-dimensional structure 3 is intended to closely fit in at least the intergluteal cleft of the body's groove. Therefore, at least a part of the three-dimensional structure 3 is located within the intergluteal cleft-facing region defined between the anus-facing reference line X2 and the coccyx-facing reference line X3.

In the sanitary napkin 1 of FIG. 1, the three-dimensional structure 3 has a front starting point 31 which is located forward of the anus-facing reference line X2 and slightly rearward of the vagina-facing reference line X1. It also has a rear starting point 32 which is located slightly forward of the coccyx-facing reference line X3.

H shown in FIG. 3 represents a height from the skin-side surface of the napkin body 2 to an apex 3a of the three-dimensional structure 3. When the sanitary napkin 1 is in a flat state, as shown in FIG. 2, the height H gradually increases toward the center from the front and rear starting points 31, 32 so that the apex 3a, which extends along the longitudinal centerline Oy of the napkin body 2, is curved away from the skin-side surface of the napkin body 2. Preferably, the apex 3a provides a maximum height $H_{max}$ at a location where the intergluteal cleft becomes deepest, i.e., within the range from the anus-facing reference line X2 to the location 50 mm rearward of it.

As shown in FIG. 3, the three-dimensional structure 3 has a pair of walls 33, 33 which extend in the longitudinal direction on opposite sides. The width between the walls 33, 33 gradually decreases from a base adjacent to the skin-side surface of the napkin body 2 toward the apex 3a. The three-dimensional structure 3 has a base width W1 which is measured at a level spaced from the skin-side surface of the napkin body 2 by h1=10 mm, and the base width W1 is preferably in the range of 15 to 45 mm. If the base width W1 is in the range of 15 to 45 mm, the three-dimensional structure 3 can enter the intergluteal cleft without giving an unpleasant feeling.

The three-dimensional structure 3 also has an apex width W2 which is measured at a level spaced from the apex 3a of the three-dimensional structure 3 by h2=3 mm, and the apex width W2 is preferably in the range of 1 to 5 mm, more preferably in the range of 1 to 3 mm. If the apex width W2 is within the range, the apex 3a can reach the deepest part of the body's groove, and particularly if the apex width W2 is equal to or greater than 1 mm, the apex 3a becomes less irritating to the body's groove even when it comes into contact with the deepest part of the body's groove.

The maximum height $H_{max}$ of the three-dimensional structure 3 is preferably in the range of 25 to 60 mm. Within this range, the apex 3a of the three-dimensional structure 3 can reach the deepest part of the intergluteal cleft.

The walls 33, 33 of the three-dimensional structure 3 form an opening angle θ which is equal to or less than 120 degrees, preferably equal to or less than 90 degrees. More preferably, it is equal to or less than 60 degrees or 45 degrees. It should be noted that when the three-dimensional structure 3 has a triangular cross-section as shown in FIG. 3, the opening angle θ is an angle between the outer surfaces of the walls 33, 33. On the other hand, when the outer surfaces of the walls 33, 33 are outwardly curved to bulge laterally in the cross-section of FIG. 3, the opening angle θ is an angle between tangents to the outer surfaces of the walls 33, 33 at one half the height from the skin-side surface of the napkin body 2 to the apex 3a.

Here, the measurement of the angle θ is carried out using a measurement jig whose cylindrical inner surface has a radius of 110 mm such that the garment-side surface of the sanitary napkin 1 is adhered to the cylindrical inner surface with the longitudinal direction of the sanitary napkin 1 being oriented along the direction of curvature of the cylindrical inner surface. Then, the angle θ is measured at a location where the bulging height of the three-dimensional structure 3 from the skin-side surface of the napkin body 2 is brought to a maximum.

Here, the cross-sectional shape of the three-dimensional structure 3 is not limited to the triangle shown in FIG. 3; for example, the apex 3a may be flattened or the walls 33, 33 may be bulged laterally outwardly to have curved surfaces.

At their lower ends, as shown in FIGS. 1 and 3, the walls 33, 33 of the three-dimensional structure 3 are integrally formed with joining members 34, and the joining members 34 are bonded to and fixed on the skin-side surface of the napkin body 2 through a hot-melt type adhesive. In the present embodiment, the three-dimensional structure 3 is so fixed as not to be removable from the skin-side surface throughout the length. However, the three-dimensional structure 3 may be fixed on the skin-side surface exclusively at locations adjacent the front and rear starting points 31, 32 so as to allow the intermediate portion to be freely movable in the width direction with respect to the skin-side surface. With this construction, the three-dimensional structure 3 can be easily kept in close contact with the intergluteal cleft even when the napkin body 2 moves laterally together with an undergarment.

As shown in FIG. 3, the three-dimensional structure 3 is composed of a reinforcing member 35 and a liquid-permeable sheet 36 covering the skin-side surface of the reinforcing member 35. The reinforcing member 35 has not only a function of increasing stiffness but also a function of absorbing and retaining liquid. Here, the three-dimensional structure 3 is hollow.

The reinforcing member 35 may be formed of an air-laid nonwoven fabric. The air-laid nonwoven fabric may be produced such that 30 wt. % of pulp fibers and 70 wt. % of sheath/core bicomponent synthetic fibers (core is polypropylene resin; sheath is polyethylene resin) are blended, deposited by the air-laid process, and pressed between heating rollers to be bonded together through a bonding force of the polyethylene resin when subjected to heat. The reinforcing member 35 may have a basis weight of about 60 to 300 g/m². Alternatively, the reinforcing member 35 may be formed of an air-laid nonwoven fabric (air-laid pulp) which is produced such that 70 wt. % or more of pulp and 30 wt. % or less of synthetic resin fibers are deposited by the air-laid process, and bonded together through a binder.

As shown in FIGS. 4 and 5, the reinforcing member 35 is heated under pressure by embossing to have compressed high-density portions 37. The high-density portions 37 are spaced in the longitudinal direction and parallel to each other to extend upward from the skin-side surface of the napkin body 2 to the apex 3a in a direction substantially perpendicular to the longitudinal direction. In the reinforcing member 35, therefore, the high-density portions 37 where the reinforcing member 35 is compressed by embossing alternate longitudinally with low-density portions 38 where the reinforcing member 35 is not compressed by embossing.

In FIG. 3, the walls 33, 33 are separately formed of the reinforcing member 35, bonded to each other at the apex 3a through a hot-melt type adhesive and then covered with the single liquid-permeable sheet 36. The liquid-permeable sheet 36 may be a through-air bonded nonwoven fabric of heat-fusible synthetic resin fibers, and the liquid-permeable sheet 36 and the reinforcing member 35 are bonded to each other through a hot-melt type adhesive applied to such an extent as not to interfere with liquid passage.

The liquid-permeable sheet 36 may be a point-bonded nonwoven fabric, a spunlaced nonwoven fabric or a spun-bonded nonwoven fabric, without limited to the through-air bonded nonwoven fabric, but its fiber density is preferably equal to or less than 0.12 g/cm³ so as to improve liquid permeability.

For the reinforcing member 35, alternatively, there may be used a through-air bonded, point-bonded or spunbonded nonwoven fabric of one or more kinds of fibers selected from polyethylene fibers, polypropylene fibers, polyester fibers, polyethylene-polypropylene bicomponent synthetic fibers and polyethylene-polyester bicomponent synthetic fibers. Two or more sheets of the nonwoven fabric may be stacked to have a basis weight, for example, of about 60 to 300 g/m² and bonded together by heat-embossing or through a hot-melt adhesive. The reinforcing member 35 thus made only of synthetic resin fibers allows passage of menstrual blood toward the liquid absorbent layer 22, and moreover because the reinforcing member 35 itself is resistant to absorption and retention of menstrual blood, menstrual blood is less apt to remain in the three-dimensional structure 3, so that the three-dimensional structure 3 is prevented from feeling sticky to the skin and provides an improved touch when in contact with the intergluteal cleft.

Along the apex 3a of the three-dimensional structure 3, as shown in FIG. 5, an elastic member 39 is fixed on the inner side of the reinforcing member 35. The elastic member 39 may be, for example, a polyurethane elastic string having a fineness of 3760 dtex. The elastic member 39 is oriented in the longitudinal direction of the three-dimensional structure 3 between the front and rear starting points 31, 32. If desired, a plurality of elastic members 39 may be arranged at spaced intervals in place of such a single elastic member 39. Along the apex 3a, the elastic member 39 is bonded to the reinforcing member 35 through a hot-melt type adhesive 41. More specifically, the elastic member 39 is bonded to the reinforcing member 35 while being stretched to about 1.2 to 1.5 times a length as measured between the front and rear starting points 31, 32 along the apex 3a when the three-dimensional structure 3 is in the state of FIG. 2.

In an alternative, the reinforcing member 35 may be formed by laminating two sheets of the air-laid nonwoven fabric or the laminated nonwoven fabric, wherein the elastic member 39 may be disposed between the two sheets along the apex 3a and then bonded to the two sheets by embossing for forming the high-density portions.

Here, the three-dimensional structure 3 may be formed by folding the air-laid nonwoven fabric or the laminated nonwoven fabric in a reversed V-shape to have the fold line located at the apex 3a.

On the garment-side surface of the napkin body 2, as shown in FIG. 3, pressure-sensitive adhesive layers 25, 25 are disposed on an outer surface of the backsheet 21. The pressure-sensitive adhesive layers 25, 25 are in the shape of strips extending continuously in the longitudinal direction. Preferably, the pressure-sensitive adhesive layers 25, 25 are located beneath the joining members 34 of the three-dimensional structure 3. With this arrangement, the napkin body 2 can be firmly fixed to an undergarment beneath the joining members 34 to keep the three-dimensional structure 3 in close contact with the intergluteal cleft.

Although omitted in the drawings, it should be noted that the fold-back flaps 7, 7 and the rear flaps 8, 8 also have pressure-sensitive adhesive layers on the garment-side surface of the backsheet 21.

When using the sanitary napkin 1, the pressure-sensitive adhesive layers 25, 25 on the garment-side surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment-side surfaces of the fold-back flaps 7, 7 are adhered to the outer side of the crotch part. In addition, the pressure-sensitive adhesive layers on the garment-side surfaces of the rear flaps 8, 8 are adhered to the inner side of the undergarment at a lower part of a back body.

When the sanitary napkin 1 is adhered to the undergarment by a user, the center location between the fold-back flaps 7, 7 (the vagina-facing reference line X1) serves as a target for positioning so that it is worn with the center location almost coinciding with the longitudinal center of the vaginal opening.

In a state where the sanitary napkin 1 is fixed to an undergarment, the elastic member 39 provided along the apex 3a of the three-dimensional structure 3 is allowed to elastically contract as shown in FIG. 5(B). The elastic member 39 is bonded to the reinforcing member 35 through the hot-melt type adhesive 41, but when the elastic member 39 contracts as shown in FIG. 5(B), the bond between the high-density portions 37 and the elastic member 39 is broken and the high-density portions 37 is brought closer to each other to deform the low-density portions 38, so that the reinforcing member 35 forms pleats along the apex 3a of the three-dimensional structure 3. As a result, the three-dimensional structure 3 is shortened in the longitudinal direction.

On the other hand, since the three-dimensional structure 3 is not subjected to such a longitudinal contractive force on the side adjacent to the skin-side surface of the napkin body 2, the napkin body 2 is allowed to be easily curved. In the sanitary napkin 1, since the elastic contractive force of the elastic member 39 also acts to bring the front and rear starting points 31, 32 closer to each other, the napkin body 2 can also be curved by this force to have its skin-side surface recessed.

When the sanitary napkin 1 is curved as shown in FIG. 4, the length as measured between the front and rear starting points 31, 32 along the apex 3a of the three-dimensional structure 3 is preferably 60% to 90%, more preferably 70% to 85% of a length as measured between the front and rear starting points 31, 32 along the skin-side surface of the napkin body 2.

Figure 13:
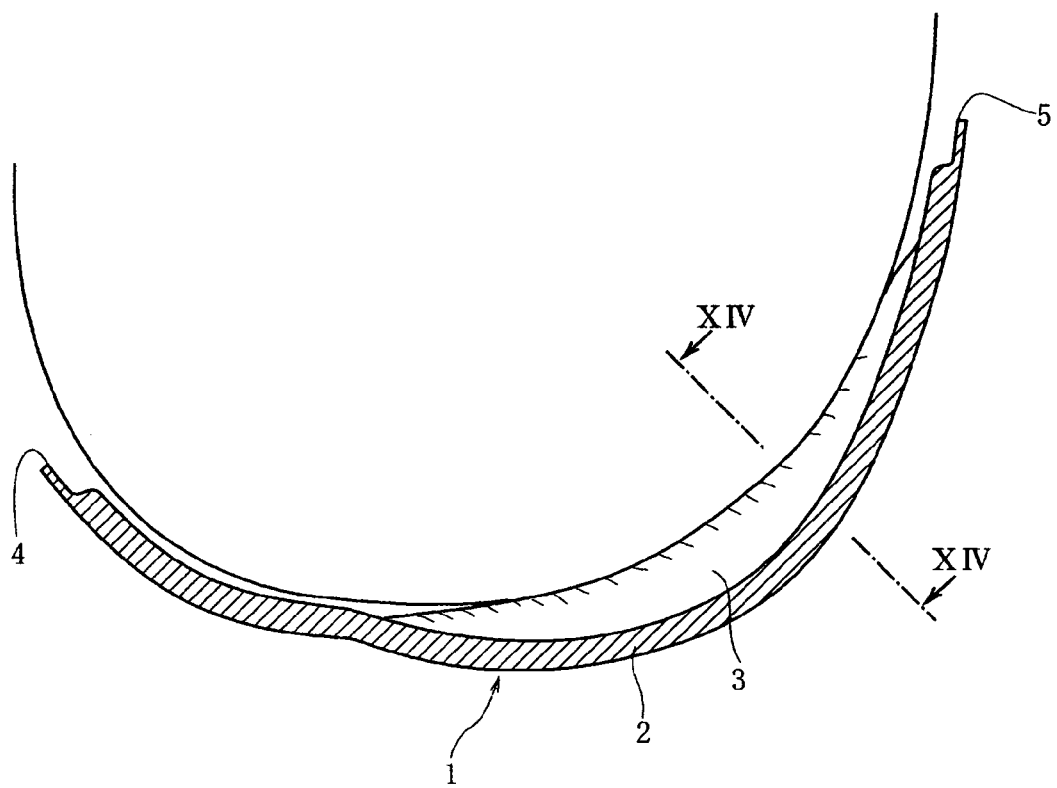
FIG. 13 is a longitudinal sectional view showing a state where the sanitary napkin of the present invention is worn in the crotch of a woman.
Figure 14:
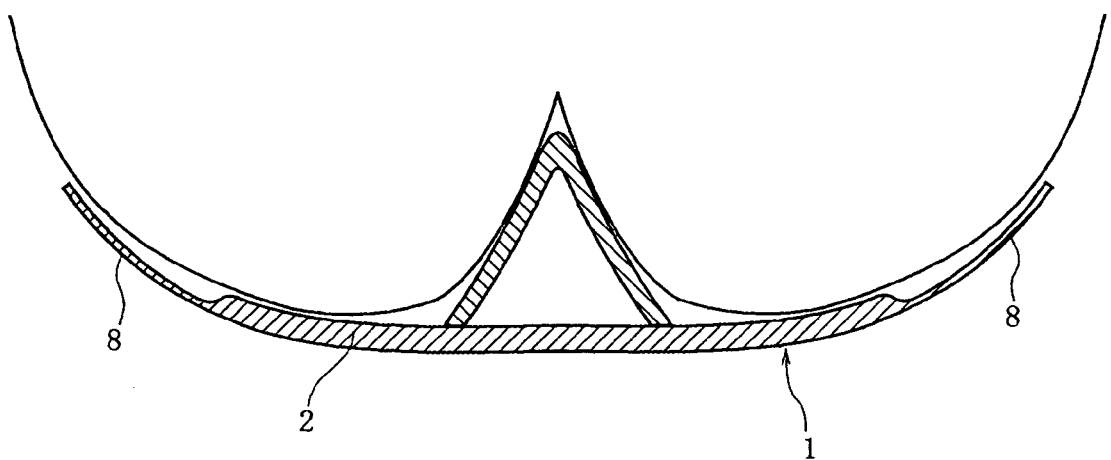
FIG. 14 is a sectional view taken along line XIV-XIV of FIG. 13.

FIG. 13 shows a state where the sanitary napkin 1 is worn in the crotch of a woman, and FIG. 14 is a sectional view taken along line XIV-XIV of FIG. 13 and shows a state where the three-dimensional structure 3 fits in the intergluteal cleft.

As shown in FIG. 3, the three-dimensional structure 3 is so shaped that the width between the walls 33, 33 gradually decreases toward the apex 3a, wherein the apex width W2 is in the range of 1 to 5 mm, preferably in the range of 1 to 3 mm. On the other hand, the opening angle θ between the walls 33, 33 is equal to or less than 90 degrees, preferably equal to or less than 60 degrees, more preferably equal to or less than 45 degrees.

Accordingly, the three-dimensional structure 3 can easily enter and fit in the body's groove from a location slightly posterior of the center of the vaginal opening to a location slightly anterior of the coccyx. In the three-dimensional structure 3, the reinforcing member 35, which is formed of an air-laid nonwoven fabric or the like to have a basis weight in the range of 60 to 300 g/m², is in itself elastic and stiff and is also formed with the high-density portions 37 extending in a direction substantially perpendicular to the longitudinal direction. Hence, the reinforcing member 35 fitting in the intergluteal cleft is less apt to be crushed down. In addition, since the reinforcing member 35 is allowed to be elastically deformed by a pressure exerted on the apex 3a, it can follow the change in the depth of the body's groove and be kept in close contact with the body groove anteriorly and posteriorly of the body. Furthermore, since the three-dimensional structure 3 is hollow, its width can freely change even when the opposing surfaces of the buttocks approach each other in the body's groove.

While the three-dimensional structure 3 is sufficiently stiff to enter the intergluteal cleft as set forth above, the napkin body 2 is allowed to be curved so that the skin-side surface of the napkin body 2 can conform to the contour of the wearer's body from the crotch to the buttocks as shown in FIG. 13. Accordingly, there is not too much clearance between the wearer's body and the skin-side surface of the napkin body 2, which effectively prevents leakage of menstrual blood.

According to the foregoing embodiment, even after the apex 3a of the three-dimensional structure 3 is shortened to curve the napkin body 2, the apex 3a remains curved to project away from the skin-side surface of the napkin body 2, as shown in FIG. 4. Therefore, the apex 3a can easily reach the deepest part of the intergluteal cleft.

When a wearer is in the standing position, for example, menstrual blood discharged from the vaginal opening passes through the topsheet 23 of the napkin body 2 and is then absorbed and retained by the liquid absorbent layer 22. However, menstrual blood trying to move posteriorly along the intergluteal cleft such as during sleep is given to the three-dimensional structure 3 in close contact with the body's groove and then absorbed by the reinforcing member 35 having the function of absorbing liquid after passing through the liquid-permeable sheet 36. If the reinforcing member 35 is formed of an air-laid nonwoven fabric containing synthetic resin fibers in an amount of 70 wt. %, menstrual blood given to the reinforcing member 35 can be readily transferred to the liquid absorbent layer 22. Accordingly, the reinforcing member 35 preferably contains synthetic resin fibers in an amount equal to or greater than 50 wt. %. If the reinforcing member 35 is made only of synthetic resin fibers, as set forth above, menstrual blood is less apt to remain in the three-dimensional structure 3.

Figure 6:
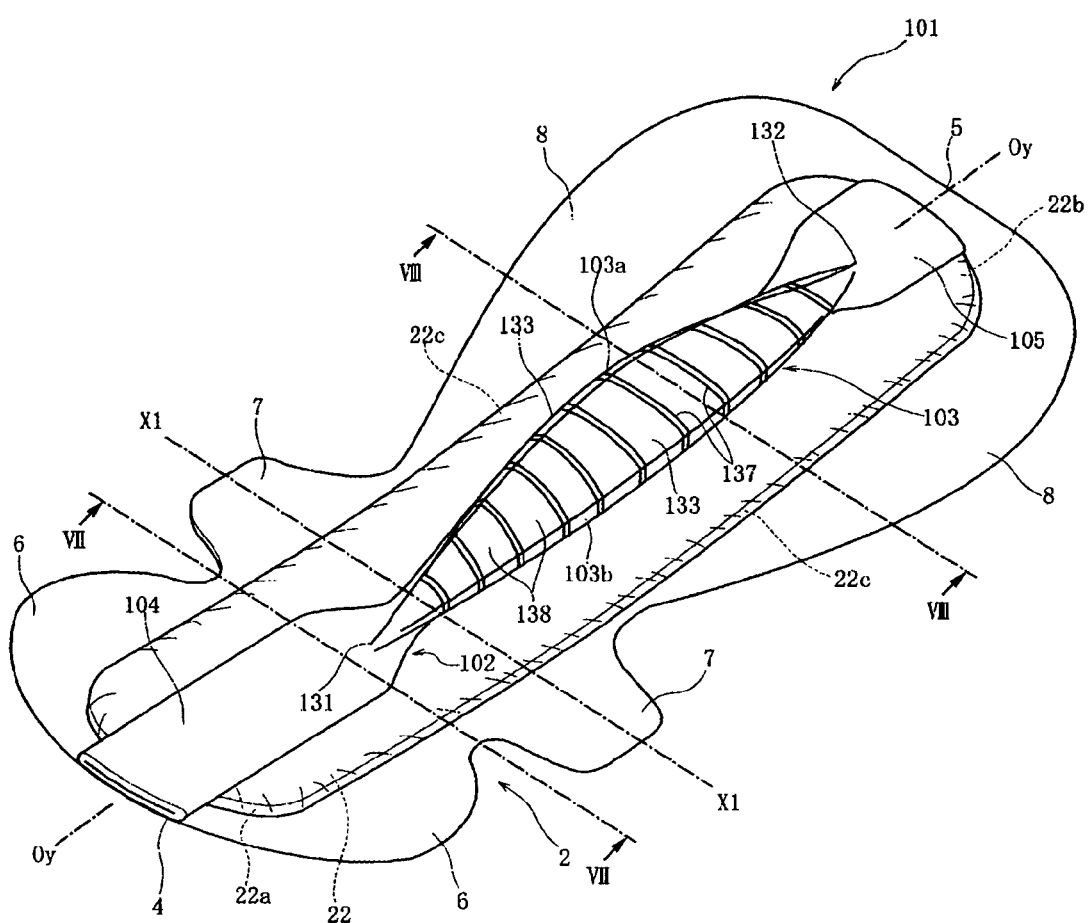
FIG. 6 is a perspective view showing a sanitary napkin according to a second embodiment of the present invention.
Figure 7:
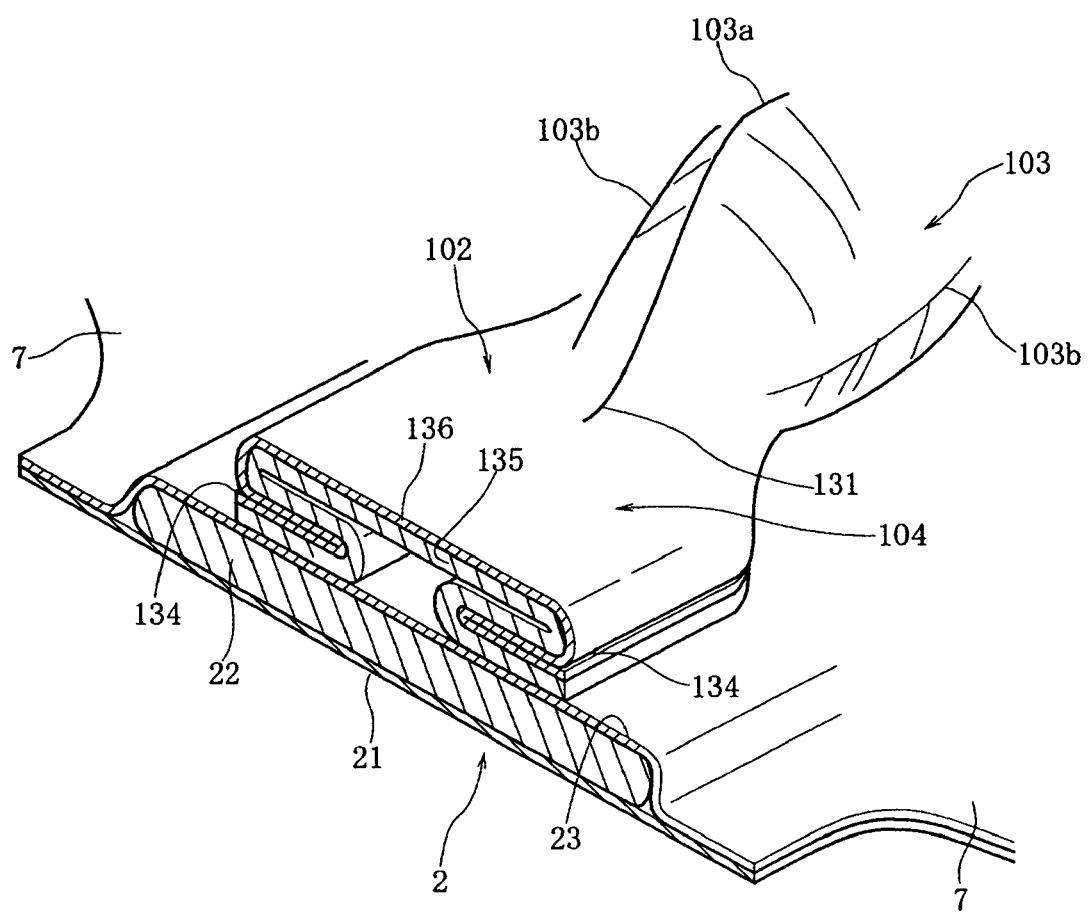
FIG. 7 is a sectional view taken along line VII-VII of FIG. 6.
Figure 8:
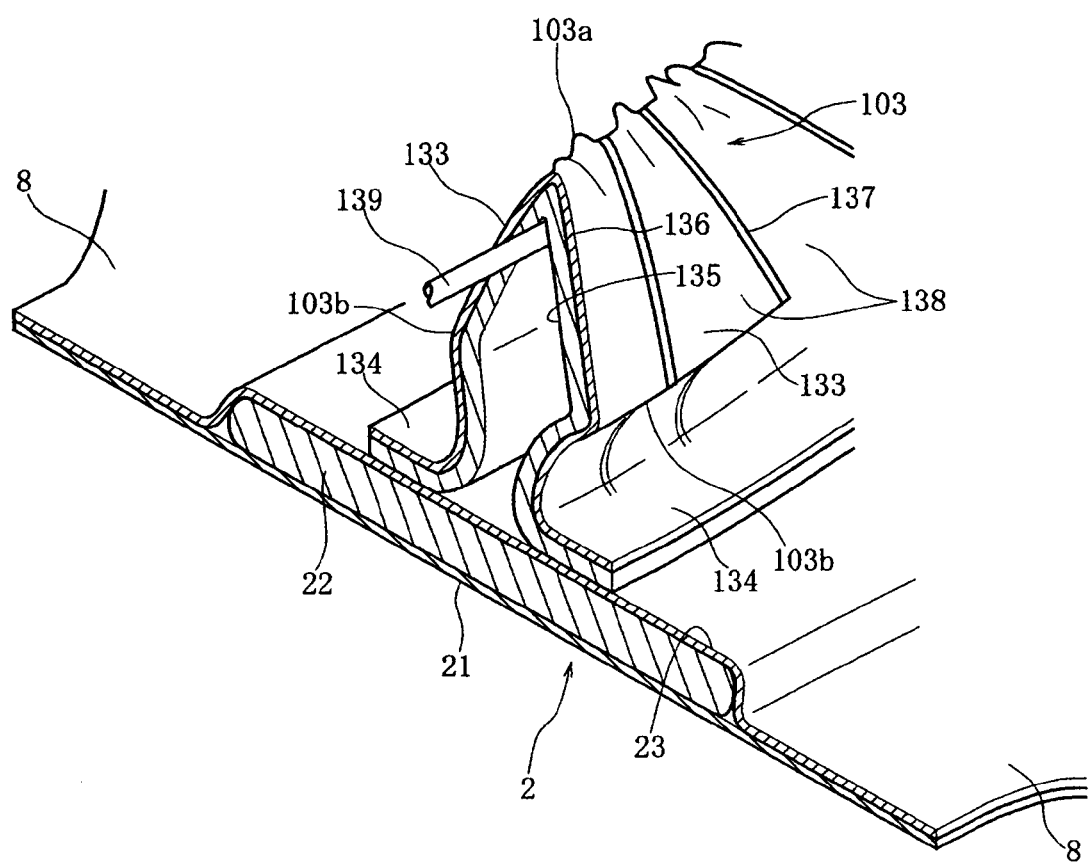
FIG. 8 is a sectional view taken along line VIII-VIII of FIG. 6.

FIG. 6 is a perspective view showing a sanitary napkin 101 according to a second embodiment of the present invention, FIG. 7 is a transverse sectional view of the sanitary napkin 101 of FIG. 6 taken along line VII-VII, and FIG. 8 is a transverse sectional view of the sanitary napkin 101 of FIG. 6 taken along line VIII-VIII.

The napkin body 2 of FIG. 6 is not changed from the napkin body of the first embodiment shown in FIGS. 1 to 3.

In the second embodiment, a surface element 102 is mounted on the skin-side surface of the napkin body 2 to extend along the longitudinal centerline Oy. As shown in FIGS. 7 and 8, the surface element 102 is composed of a reinforcing member 135 having the function of absorbing liquid and a liquid-permeable sheet 136 covering the skin-side surface of the reinforcing member 135. The reinforcing member 135 is formed of an air-laid nonwoven fabric of pulp and synthetic resin fibers, wherein the content of the synthetic resin fibers is equal to or greater than 50 wt. %, e.g., 70 wt. %. A single sheet of the air-laid nonwoven fabric may be used or two or more sheets may be stacked to form walls 133, 133. In an alternative, the reinforcing member 135 may be formed by joining two or more sheets of a nonwoven fabric made only of synthetic resin fibers, as set forth above.

The liquid-permeable sheet 136 is formed of the same through-air bonded nonwoven fabric as used for the liquid-permeable sheet 36. Here, the reinforcing member 135 and the liquid-permeable sheet 136 are bonded to each other through a hot-melt type adhesive applied to such an extent as not to interfere with liquid passage.

Between front and rear starting points 131, 132, the surface element 102 forms a three-dimensional structure 103, as shown in FIG. 6. As shown in FIG. 8, the three-dimensional structure 103 is hollow and the width between the walls 133, 133 gradually increases from an apex 103a toward the napkin body 2 to provide protrusion apexes 103b, 103b, between which the width is brought to a maximum, at a level spaced upward from the skin-side surface of the napkin body 2 by 10 mm or more. Then, the width gradually decreases from the left and right protrusion apexes 103b, 103b to the skin-side surface of the napkin body 2. At its base, moreover, the three-dimensional structure 103 extends laterally to provide joining members 134, 134 throughout the length of the three-dimensional structure 103, and the joining members 134, 134 are bonded to and fixed on the skin-side surface of the napkin body 2 through a hot-melt type adhesive.

In the reinforcing member 135 of the three-dimensional structure 103, high-density portions 137 where the reinforcing member 135 is compressed by embossing alternate longitudinally with low-density portions 138 where the reinforcing member 135 is not compressed by embossing. The compressed portions 137 are formed in the walls 133, 133 to extend from the skin-side surface of the napkin body 2 to the apex 103a in a direction substantially perpendicular to the longitudinal direction. The compressed portions 137 are spaced in the longitudinal direction and extend parallel to each other.

Also between the front and rear starting points 131, 132, an elastic member 139 in a stretched state is bonded to the inner side of the reinforcing member 135 along the apex 103a.

In the three-dimensional structure 103, the front starting point 131 is located 10 to 20 mm forward of the vagina-facing reference line X1, while the rear starting point 132 is located slightly forward of the coccyx-facing reference line X3. Thus, the three-dimensional structure 103 can be brought into close contact with the wearer's body from the region posterior to the vaginal opening to the intergluteal cleft.

Forward of the front starting point 131, as shown in FIGS. 7 and 8, the surface element 102 is folded flat and substantially entirely fixed to the skin-side surface of the napkin body 2 to provide a front flattened portion 104. As also seen from FIG. 6, a rear flattened portion 105 is likewise formed rearward of the rear starting point 132.

In the sanitary napkin 101 according to the second embodiment, the length of the apex 103a is decreased by an elastic contractive force of the elastic member 139 to form pleats along the apex 103a. Accordingly, the napkin body 2 can be curved while the three-dimensional structure 103 is kept bulging with a sufficient stiffness, as in the first embodiment.

Moreover, the protrusion apexes 103b, 103b are provided in the walls 133, 133 of the three-dimensional structure 103 and above them, the width of the three-dimensional structure 103 gradually decreases toward the apex 103a. When the sanitary napkin 101 is worn in the crotch, accordingly, the portion above the protrusion apexes 103b, 103b is allowed to come into close contact with the body's groove. With the protrusion apexes 103b, 103b, moreover, the three-dimensional structure 103 is allowed to be easily deformed toward the skin-side surface of the napkin body 2 by a pressure exerted on the apex 3a. This enables the three-dimensional structure 103, which is in close contact with the body's groove, to be freely deformed when the depth of the body's groove changes during sleep.

Since the three-dimensional structure 103 is designed to come into close contact with the labia at a location adjacent the front starting point 131, menstrual blood discharged from the vaginal opening can be immediately collected by the three-dimensional structure 103. In addition, since the front flattened portion 104 is designed to come into close contact with the anterior part of the vaginal opening, the degree of adhesion to the vaginal opening is improved in this part, so that menstrual blood can be collected by the reinforcing member 135 to effectively prevent lateral leakage of menstrual blood.

Figure 9:
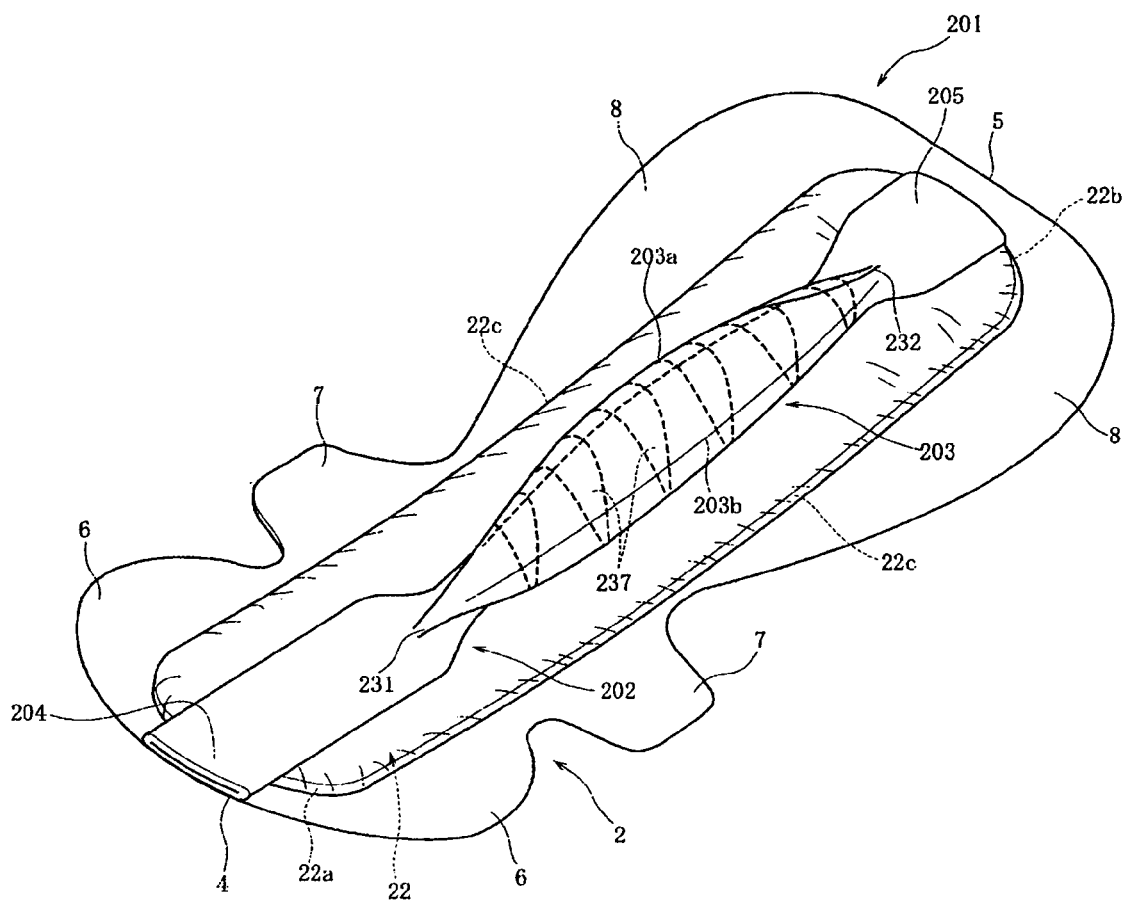
FIG. 9 is a perspective view showing a sanitary napkin according to a third embodiment of the present invention.
Figure 10A:
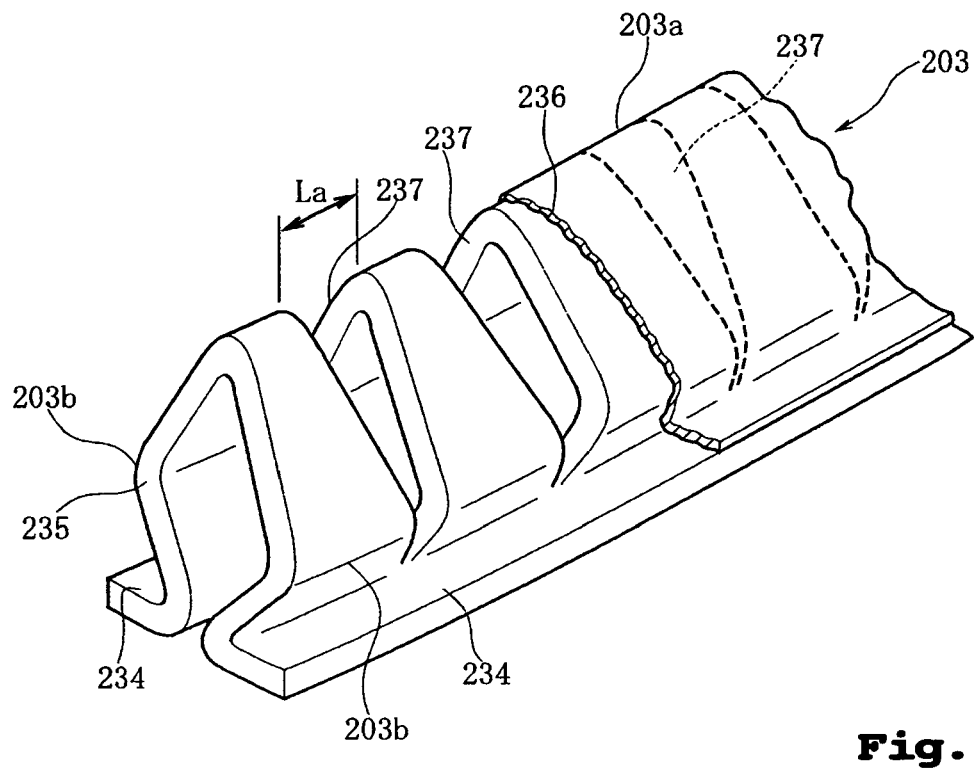
Figure 10B:
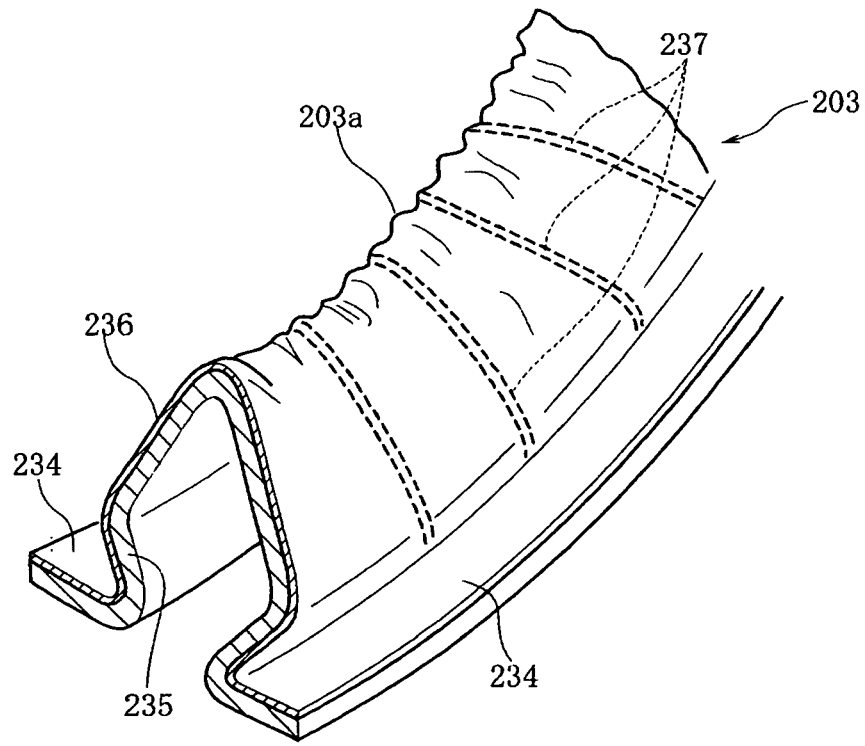

FIG. 9 is a perspective view showing a sanitary napkin 201 according to a third embodiment of the present invention, and FIGS. 10(A) and 10(B) are partially broken perspective views of a three-dimensional structure provided in the sanitary napkin 201.

The napkin body 2 of the sanitary napkin 201 is identical to the napkin bodies employed in the sanitary napkin 1 according to the first embodiment and the sanitary napkin 101 according to the second embodiment.

On the skin-side surface of the napkin body 2 is provided a surface element 202. As shown in FIGS. 10(A) and 10(B), the surface element 202 is composed of a reinforcing member 235 having the function of absorbing liquid and a liquid-permeable sheet 236 covering the skin-side surface of the reinforcing member 235. The reinforcing member 235 may be formed of an air-laid nonwoven fabric as in the first and second embodiments. The liquid-permeable sheet 236 may also be identical to those used in the foregoing embodiments.

At its base, the surface element 202 has joining members 234, 234 bonded to and fixed on the skin-side surface of the napkin body 2 through a hot-melt type adhesive. The surface element 202 is folded in the same manner as shown in FIG. 7 to provide a front flattened portions 204 forward of a front starting point 231 and a rear flattened portions 205 rearward of a rear starting point 232. Between the front and rear starting points 231, 232, the surface element 202 provides a three-dimensional structure 203 which rises away from the skin-side surface of the napkin body 2, as shown in FIG. 9.

As shown in FIG. 10(A), the reinforcing member 235 has a plurality of cut-outs (or notches) 237 spaced apart in the longitudinal direction of the sanitary napkin 201. A longitudinal opening size La of the individual cut-outs 237 is maximum at the apex 203a of the three-dimensional structure 203 and gradually decreases toward the joining members 234, 234. The cut-outs 237 may be formed by cutting out portions of the reinforcing member 235 before or after folding the reinforcing member 235 into the shape having the apex 203a and protrusion apexes 203b.

The cut-outs 237 are not visible externally because the reinforcing member 235 is covered with the liquid-permeable sheet 236.

When the napkin body 2 is in a flat state, the cut-outs 237 of the reinforcing member 235 remains opened, as shown in FIG. 10(A). When the napkin body 2 is curved to conform to the contour of the wearer's body from the crotch to the buttocks, on the other hand, the cut-outs 237 are narrowed to bring the distinct portions of the reinforcing member 235 closer to each other or into close contact with each other, thereby shortening the apex 203a of the three-dimensional structure 203, as shown in FIG. 10(B).

Accordingly, when the napkin body 2 is in a curved state, the three-dimensional structure 203 hardly exerts a compression restoring force to restore the napkin body 2 to its original flat state, so that the napkin body 2 can be kept curved while the three-dimensional structure 203 is in close contact with the intergluteal cleft.

Figure 11A:
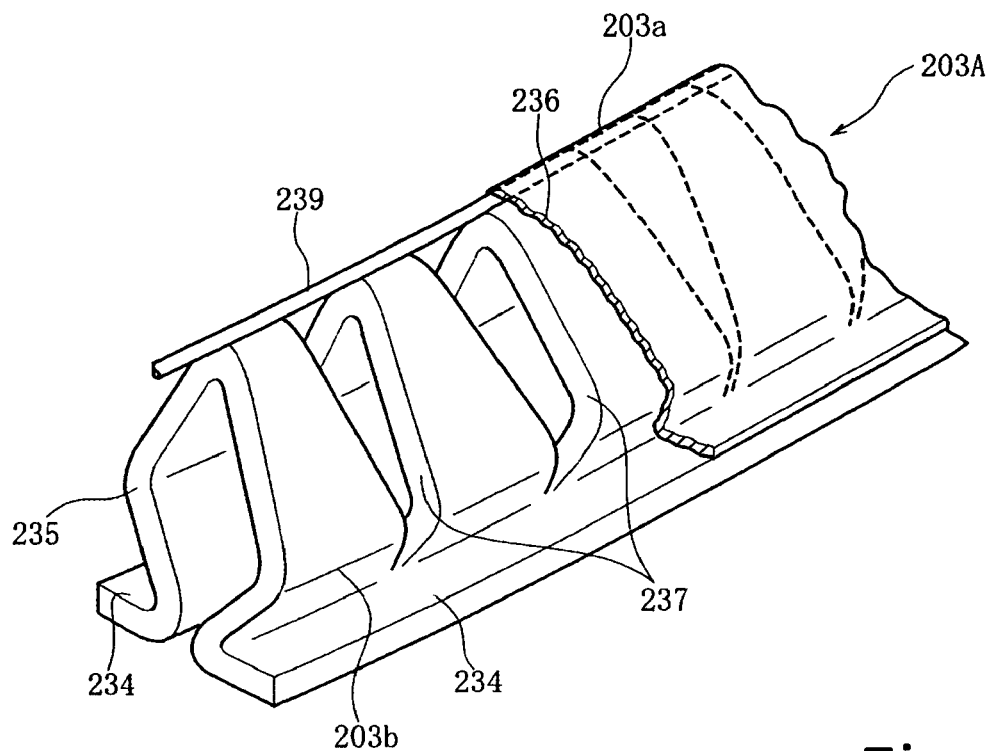
Figure 11B:
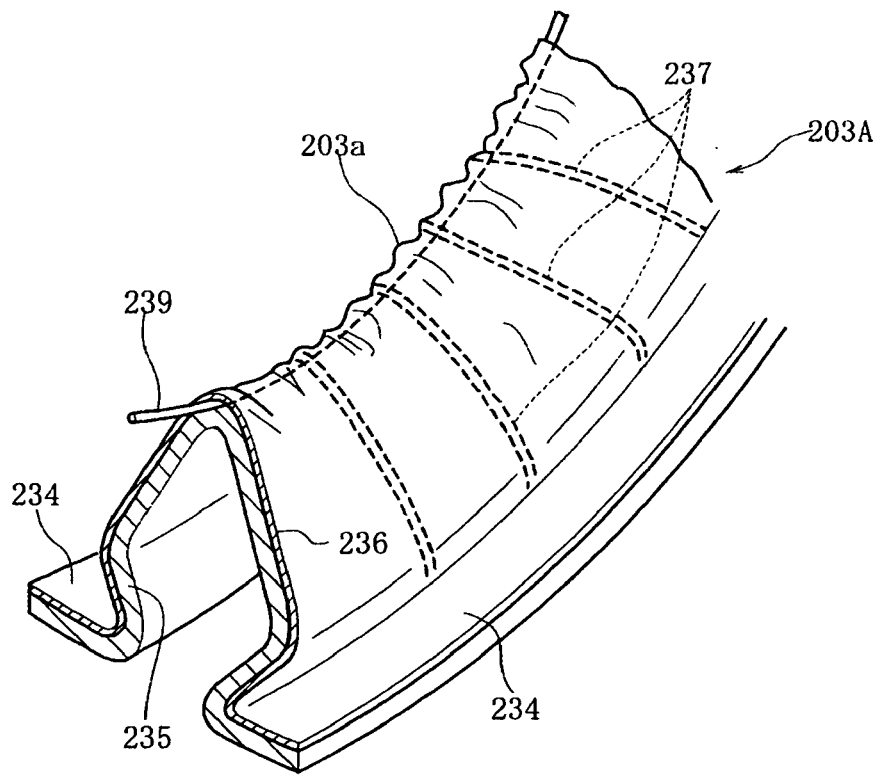

FIGS. 11(A) and 11(B) show modifications of the third embodiments of the present invention.

FIGS. 11(A) and 11(B) shows a three-dimensional structure 203A, in which an elastic member 239 for exhibiting an elastic contractive force in the longitudinal direction is provided between the liquid-permeable sheet 236 and the reinforcing member 235 having the cut-outs 237 to extend along the apex 203a.

In this modification, the elastic member 239 exerts an elastic force to bring the front and rear starting points 231, 232 closer to each other in a state where no external force is working on the sanitary napkin 201, so that the napkin body 2 is curved and at the same time, the cut-outs 237 are narrowed to shorten the apex 203a, as shown in FIG. 11(B).

It should be noted that in the second embodiment shown in FIGS. 9 and 10, the cut-outs 237 may be exposed externally without being covered with the liquid-permeable sheet 236.

Also in the second embodiment, the distinct portions of the reinforcing member 235 may be completely separated from each other by the cut-outs 237.

It should also be noted that in the foregoing embodiments, the apex of the three-dimensional structure is designed to be curved away from the skin-side surface of the napkin body 2 even after the napkin body 2 is curved to conform to the contour of the wearer's body, as shown in FIG. 4, but if desired, the apex may be concavely curved when the napkin body 2 is curved as shown in FIG. 4.

The present invention should not be understood as limited to the foregoing embodiments, but various other changes may be made therein. For example, the reinforcing members 35, 135, 235 according to the foregoing embodiments have the function of absorbing liquid, but the three-dimensional structure may include an additional liquid absorbent layer or a cushion layer separately from the reinforcing member.

Figure 12A:
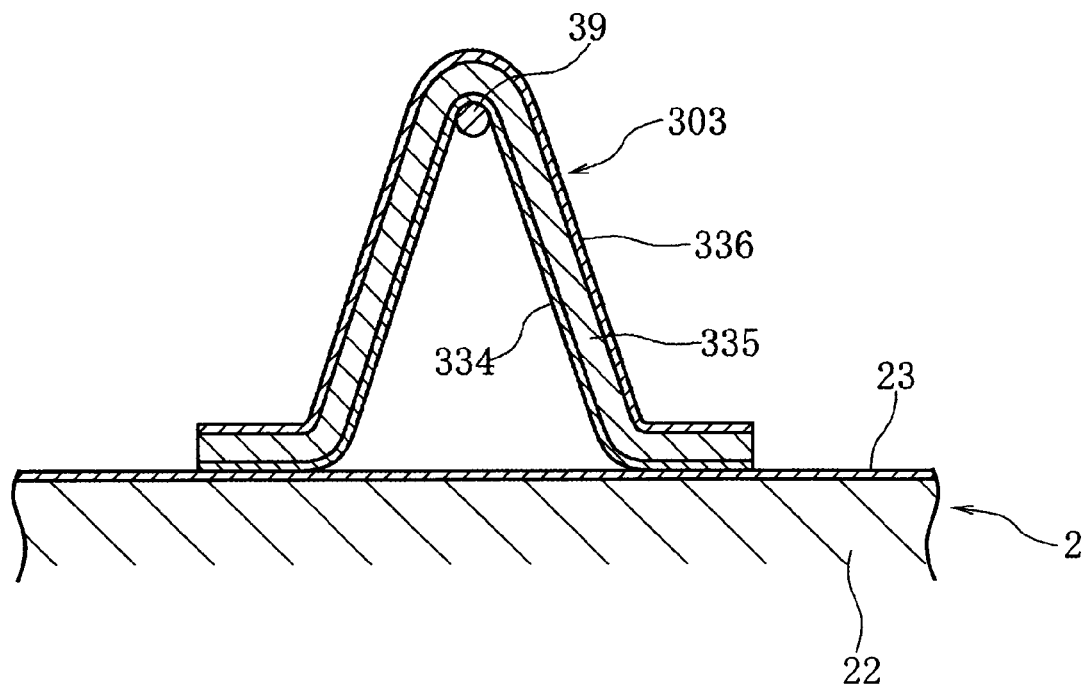
FIGS. 12(A) and 12(B) are transverse sectional views showing three-dimensional structures according to different embodiments.

FIG. 12(A) shows a three-dimensional structure 303 in which a reinforcing member 334 is bonded to the inner surface of a liquid absorbent layer 335 which may be formed of an air-laid nonwoven fabric having the function of absorbing liquid, an air-laid nonwoven fabric only of pulp (air-laid pulp), a paper, or a spunlaced nonwoven fabric of rayon fibers. The reinforcing member 334 may be a paper, a urethane foam sheet, a polyethylene foam sheet, or a resin sheet. On the other hand, the outer surface of the liquid absorbent layer 335 is covered with a liquid-permeable sheet 336.

Figure 12B:
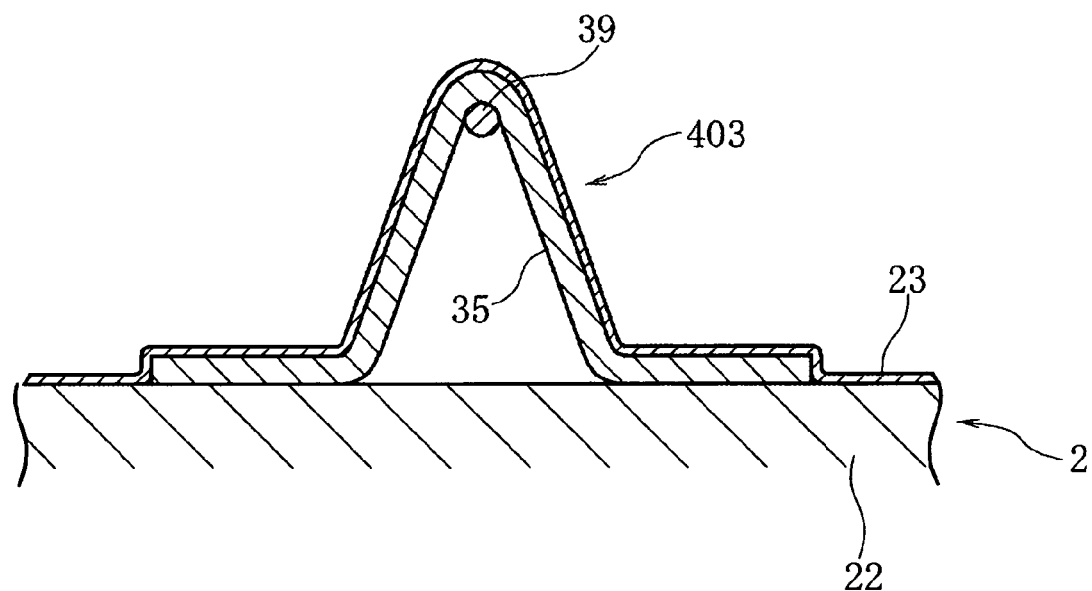

FIG. 12(B) shows a three-dimensional structure 403 in which the reinforcing member 35, which is not changed from that used in the first embodiment, is covered with the topsheet 23.

The three-dimensional structures according to the foregoing embodiments have a sufficient stiffness in itself to maintain the three-dimensional shape bulging from the skin-side surface of the napkin body 2 and are also allowed to be elastically deformed by a pressure exerted on the apex.

In the case where the elastic member is not provided, if the reduction in height is equal to or less than 66% when a pressure of 0.2 N per unit area having a width of 1 mm and a length of 10 mm is applied to the apex at the location where the three-dimensional structure has the maximum height $H_{max}$, the three-dimensional structure can be kept in close contact with at least a noncontact portion (where the opposing surfaces of the buttocks are separated from each other) in the most part of the body's groove even when the wearer alters her position from the standing position to the supine position.

In the case where the elastic member is not provided, if the reduction in height at the apex is equal to or greater than 20% when a force of 0.3 N per unit area having a width of 1 mm and a length of 10 mm is applied to the apex at the location where the three-dimensional structure has the maximum height $H_{max}$, the three-dimensional structure does not give an unpleasant feeling to the wearer even when the depth of the body's groove varies during sleep, so that the three-dimensional structure can be kept in close contact with the body's groove.

The present invention should not be understood as limited to the specific embodiments set out above but to include all possible embodiments which can be embodied within a scope encompassed and equivalent thereof with respect to the features set out in the appended claims.

What is claimed is:

1. A sanitary napkin comprising a napkin body containing a liquid absorbent layer for absorption and retention of liquid and a three-dimensional structure disposed on a skin-side surface of the napkin body, wherein
   the three-dimensional structure includes a reinforcing member and a liquid-permeable sheet covering a skin-side surface of the reinforcing member, the reinforcing member acting to keep the three-dimensional structure bulging from the skin-side surface of the napkin body and capable of being deformed by a load exerted on the three-dimensional structure, wherein
   the reinforcing member forms two walls opposing in a width direction of the sanitary napkin with a hollow therebetween,
   the reinforcing member is formed of a fibrous layer,
   a width of the reinforcing member decreases toward an apex of the reinforcing member, the apex extending in a longitudinal direction of the sanitary napkin,
   the reinforcing member having high-density portions and low-density portions formed in the two walls, such that the low-density portions have a density that is lower than the high-density portions and alternate with the high-density portions along the longitudinal direction of the sanitary napkin, the high-density portions each extending linearly from the skin-side surface of the napkin body to the apex of the reinforcing member,
   an elastic member is affixed at the apex of the reinforcing member, and
   when front and rear ends of the three-dimensional structure are brought closer to each other with the skin-side surface of the napkin body concavely curved by a longitudinal contractive force of the elastic member, the low density portions deform allowing the high density portions to be brought closer to one another at the apex, and such that a length of the reinforcing member along the apex decreases more than a length of the reinforcing member along the skin-side surface of the napkin body.

2. The sanitary napkin of claim 1, wherein the elastic member is provided to shorten the apex of the reinforcing member in the longitudinal direction of the sanitary napkin.

3. The sanitary napkin of claim 1, wherein the napkin body is elongated to have a vagina-facing region and an intergluteal cleft-facing region rearward of the vagina-facing region and the three-dimensional structure is provided at least in the intergluteal cleft-facing region.

* * * * *